US008481480B1

(12) United States Patent
Lam et al.

(10) Patent No.: US 8,481,480 B1
(45) Date of Patent: Jul. 9, 2013

(54) ANTI-ADHERENT FORMULATION INCLUDING A QUATERNARY AMMONIUM COMPOUND AND A FATTY ALCOHOL

(76) Inventors: Uyen T. Lam, Appleton, WI (US); Kelly Laura Wolff, Appleton, WI (US); Corey T. Cunningham, Larsen, WI (US); Douglas R. Hoffman, Greenville, WI (US); Scott W. Wenzel, Neenah, WI (US)

( * ) Notice: Subject to any disclaimer, the term of this patent is extended or adjusted under 35 U.S.C. 154(b) by 0 days.

(21) Appl. No.: 13/460,284

(22) Filed: Apr. 30, 2012

(51) Int. Cl.
*A61K 38/00* (2006.01)

(52) U.S. Cl.
USPC .............................. 514/1.1; 514/642; 514/17.2

(58) Field of Classification Search
None
See application file for complete search history.

(56) References Cited

U.S. PATENT DOCUMENTS

| | | | |
|---|---|---|---|
| 5,849,281 A | 12/1998 | Babinski et al. | |
| 5,925,615 A | 7/1999 | Kern et al. | |
| 5,965,610 A | 10/1999 | Modak et al. | |
| 6,024,951 A * | 2/2000 | Babinski et al. | 424/73 |
| 6,383,505 B1 | 5/2002 | Kaiser et al. | |
| 6,488,948 B1 | 12/2002 | Danieli | |
| 6,537,533 B2 | 3/2003 | Alvarado | |
| 6,638,497 B2 | 10/2003 | Barinova et al. | |
| 7,048,770 B2 | 5/2006 | Azizova et al. | |
| 7,157,389 B2 | 1/2007 | Branham et al. | |
| 7,192,601 B2 | 3/2007 | Walker | |
| 7,195,771 B1 | 3/2007 | Hsu et al. | |
| 7,268,165 B2 | 9/2007 | Greten et al. | |
| 7,556,819 B1 | 7/2009 | Bryson et al. | |
| 7,642,395 B2 | 1/2010 | Schroeder et al. | |
| 7,820,149 B2 | 10/2010 | Cunningham et al. | |
| 2002/0155962 A1 | 10/2002 | Cincotta et al. | |
| 2003/0190302 A1 | 10/2003 | Frantz et al. | |
| 2004/0009141 A1 | 1/2004 | Koenig et al. | |
| 2004/0241114 A1 | 12/2004 | Gupta | |
| 2004/0247685 A1 | 12/2004 | Modak et al. | |
| 2005/0048008 A1 | 3/2005 | Gupta | |
| 2005/0158270 A1 | 7/2005 | Frantz et al. | |
| 2005/0169879 A1 | 8/2005 | Glover et al. | |
| 2006/0057096 A1 | 3/2006 | Lazzeri et al. | |
| 2006/0140899 A1 * | 6/2006 | Koenig et al. | 424/70.27 |
| 2006/0263323 A1 | 11/2006 | Hoang et al. | |
| 2007/0110696 A1 | 5/2007 | Johnson et al. | |
| 2008/0039351 A1 | 2/2008 | Walker | |
| 2008/0095861 A1 | 4/2008 | Walker | |
| 2008/0131391 A1 | 6/2008 | Ellington et al. | |
| 2008/0286224 A1 | 11/2008 | Vega et al. | |
| 2008/0286320 A1 | 11/2008 | Vega et al. | |
| 2009/0013481 A1 | 1/2009 | Colaco et al. | |
| 2009/0016975 A1 | 1/2009 | Bianchini et al. | |
| 2009/0041820 A1 | 2/2009 | Wu et al. | |
| 2009/0053161 A1 | 2/2009 | Nguyen et al. | |
| 2009/0071493 A1 | 3/2009 | Nguyen et al. | |
| 2009/0118152 A1 | 5/2009 | Lam et al. | |
| 2009/0123578 A1 | 5/2009 | Crutchfield, III | |
| 2009/0142381 A1 | 6/2009 | Agarelli et al. | |
| 2009/0155325 A1 | 6/2009 | Wenzel et al. | |
| 2009/0226497 A1 | 9/2009 | Cunningham et al. | |
| 2009/0226498 A1 | 9/2009 | Flugge-Berendes et al. | |
| 2009/0297466 A1 | 12/2009 | Gutmann et al. | |
| 2009/0324508 A1 | 12/2009 | Bobbert | |
| 2009/0324737 A1 | 12/2009 | Walker | |
| 2010/0150971 A1 | 6/2010 | Seidling et al. | |
| 2010/0158964 A1 | 6/2010 | Cunningham et al. | |
| 2010/0158986 A1 | 6/2010 | Decker et al. | |
| 2010/0202978 A1 | 8/2010 | Gurge et al. | |
| 2010/0256033 A1 | 10/2010 | Menard et al. | |
| 2010/0261394 A1 | 10/2010 | Bradley et al. | |
| 2010/0278906 A1 | 11/2010 | Sondgeroth et al. | |

FOREIGN PATENT DOCUMENTS

| | | |
|---|---|---|
| EP | 1 800 653 B1 | 7/2008 |
| EP | 1 420 645 B1 | 11/2009 |
| EP | 1420645 B1 * | 11/2009 |
| EP | 2 216 010 A1 | 8/2010 |
| WO | WO 01/21138 A1 | 3/2001 |
| WO | WO 2009/129627 A1 | 10/2009 |
| WO | WO 2010/056685 A2 | 5/2010 |

\* cited by examiner

*Primary Examiner* — Cecilia J Tsang
*Assistant Examiner* — Zachary J Miknis
(74) *Attorney, Agent, or Firm* — R. Joseph Foster, III

(57) ABSTRACT

Formulations having anti-adherent properties are disclosed herein. The anti-adherent formulation described herein acts to prevent the adherence of menses and/or fecal material to the skin in the labial and perianal regions during and after menstruation or defecation, respectively. The anti-adherent formulation contains a carrier, from about 0.1% by weight to about 10.0% by weight of a quaternary ammonium compound, and from about 0.5% by weight to about 10.0% by weight of a fatty alcohol. The anti-adherent formulation may be applied to the targeted surface either directly, in liquid form, such as by a spray bottle or similar packaging capable of delivering a liquid formulation in a relatively uniform amount over the full surface to be covered. Alternatively, the formulation may be applied to the targeted surface by a "wet" wipe or wiper.

17 Claims, No Drawings

ANTI-ADHERENT FORMULATION INCLUDING A QUATERNARY AMMONIUM COMPOUND AND A FATTY ALCOHOL

BACKGROUND

Menses is a viscoelastic fluid composed of blood (primarily red blood cells and plasma), cervical mucus and/or tissue fragments. As menses and other non-menstrual fluids exit the vagina, they often wick along the body, causing the fluids to remain on the skin or on hair located in this region, causing the fluid to dry out and remain on the skin and/or hair. When absorbent articles are used to absorb and contain menses and other non-menstrual fluids, often the fluids do not reach the absorbent article so that the absorbent article will be able to absorb and contain the desired fluids. As a result of these fluids remaining on the skin, undesirable situations such as transfer of the fluids to undergarments, staining of undergarments, chafing, and unwanted odors may occur.

Absorbent materials and absorbent articles are known in the art and are known to have a wide variety of uses, in particular for absorbing bodily fluids. Examples of such absorbent materials and absorbent articles include, for example; personal care products, such as disposable diapers and training pants; feminine hygiene products, such as sanitary napkins and tampons; incontinent care products, such as pads and undergarments and the like. As is mentioned above, some fluids designed to be absorbed by these articles sometimes do not reach the absorbent article, and remain deposited on skin and hair.

Numerous commercially available products exist to assist individuals in cleaning themselves in the labial and perianal regions of the body. Conventional bath tissues have been used for many years and, recently, flushable moist bath tissues have been introduced. These products may be used alone, or in combination, to effectuate cleansing of the perianal and labial regions.

Proper cleaning of skin in the perianal and vaginal regions can be difficult due to the topography of the skin in that region and the presence of hair follicles. A common problem encountered by many individuals during cleaning of these areas after bowel movements or during menstruation is the occasional sticking of fecal material or menses to the skin in the perianal and labial areas. Additionally, because fecal material generally contains bacteria and active enzymes, the presence of this material in the perianal region after bowel movement cleanup can also result in skin irritation, redness, and even inflammation and infection for sensitive individuals. Residual menstrual fluid can support the accumulation of organic material which can persist with subsequent cleanings. These residues contain bacteria, yeast, enzymes, odor inducing agents, and microbial growth promoters. These factors can alone or in combination cause skin irritation, itching sensations, infections, as well as personal discomfort.

Based on the foregoing, it is clear that maintaining clean and healthy skin in the perianal, labial, and surrounding areas is difficult, yet important. As such, products that can improve cleaning of the skin in these regions are highly desirable, as are products which can aid in preventing menses and other fluids from adhering and sticking to the skin.

SUMMARY

Formulations having anti-adherent properties are disclosed herein. The anti-adherent formulation described herein acts to prevent the adherence of menses and/or fecal material to the skin in the labial and perianal regions during and after menstruation or defecation, respectively. The anti-adherent formulation contains a carrier, a quaternary ammonium compound, and a fatty alcohol.

The anti-adherent formulation may include a quaternary ammonium compound selected from behentrimonium methosulfate, behentrimonium chloride, cetrimonium chloride, $C_{10-40}$ isoalkylamidopropylethyldimonium ethosulfate, stearamidopropyl ethyldimonium ethosulfate, cocotrimonium chloride, quaternium-79 hydrolyzed collagen, quaternium-80, quaternium-88, quaternium-95, polyquaternium-68, polyquaternium-78, polyquaternium-81, polyquaternium-82, and combinations thereof. In one desirable embodiment, the quaternary ammonium compound may be behentrimonium chloride. Desirably, the anti-adherent formulation may include from about 0.1% by weight to about 10.0% by weight of the quaternary ammonium compound. More desirably, the anti-adherent formulation may include from about 0.25% by weight to about 7.0% by weight of the quaternary ammonium compound.

The anti-adherent formulation also includes a fatty alcohol. The fatty alcohol is selected from lauryl alcohol, myristyl alcohol, cetyl alcohol, cetearyl alcohol, stearyl alcohol, arachidyl alcohol, behenyl alcohol, and combinations thereof. Desirably, the fatty alcohol may have between 12 and 22 carbon atoms per molecule. In one desirable embodiment, the fatty alcohol may be cetearyl alcohol. Desirably, the anti-adherent formulation may include from about 0.5% by weight to about 10.0% by weight of the fatty alcohol.

The anti-adherent formulation may be applied to the targeted surface either directly, in liquid form, such as by a spray bottle or similar packaging capable of delivering a liquid formulation in a relatively uniform amount over the full surface to be covered. Alternatively, the formulation may be applied to the targeted surface by a wipe on a basesheet (i.e., a "wet" wipe or wiper).

These features will be described in greater detail herein. Further, it is to be understood that both the foregoing general description and the following detailed description are exemplary and are intended to provide further explanation of the invention claimed.

DETAILED DESCRIPTION

The present disclosure will be expressed in terms of its various components, elements, constructions, configurations, arrangements, and other. It is contemplated that the various forms of the disclosed invention may incorporate one or more of its various features and aspects, and that such features and aspects may be employed in any desired, operative combination thereof.

It should also be noted that, when employed in the present disclosure, the terms "comprises", "comprising", and other derivatives from the root term "comprise" are intended, to be open-ended terms that specify the presence of any stated features, elements, integers, steps, or components and are not intended to preclude the presence or addition of one or more other features, elements, integers, steps, components, or groups thereof.

Formulations having anti-adherent properties are disclosed herein. The anti-adherent formulation described herein acts to prevent the adherence of menses and/or fecal material to the skin in the labial and perianal regions during and after menstruation or defecation, respectively.

The presence of the anti-adherent formulation results in a decreased amount of menstrual and/or fecal material on the skin in the labial and/or anal region during menstruation or after a bowel movement. Without being bound to a particular theory, it is believed that the anti-adherent formulation attaches to the skin through electrostatic and hydrophobic interaction with the skin and remains tightly bound thereto after deposit. When menstruation occurs, menses, which also typically attaches to skin through electrostatic and hydrophobic interactions, is not able to make the attachment to the skin as many of the binding sites are already occupied with anti-adherent formulation. Because interaction between the menses and the skin is reduced, much less menses remains attached to the skin after menstruation The anti-adherent formulation may be applied to the target skin area by one of many different delivery vehicles. For example, the formulation may be applied with a wipe, including mitts and gloves, a solid stick formulation, an aerosol dispenser, a pump spray, a trigger spray, a squeeze bottle, as a foam, as a cream, as an ointment, as a salve, as a gel, as a wash or as a lotion. In addition, absorbent articles such as pads or pants, diapers and the like may also be used as a means to transfer the formulation to the skin. Whichever method is selected, it is desirable that the formulation be administered in an acceptable fashion to the target skin area without leaving a messy aesthetically unpleasing or uncomfortable residue on the skin. It is further desirable that the formulation be administered without direct contact with the users' or applicators' hands, which could result in a messy residue being left on the users' or applicators' hands, requiring additional clean up after application. Of the methods described above, the application with a wipe has some advantage over the other methods. For example, the wipe may be easily provided in a pouch with a disposable absorbent personal care article.

The anti-adherent formulation may be applied to the targeted surface either directly, in liquid form, such as by a spray bottle or similar packaging capable of delivering a liquid formulation in a relatively uniform amount over the full surface area to be covered. Alternatively, the formulation may be applied to the targeted surface by a carrier, such as a basesheet (i.e., a "wet" wipe or wiper). Because the formulation is liquid at room temperature, the formulation may be applied to a surface by wiping the surface with a basesheet that has been saturated with the formulation; the formulation will transfer from the basesheet to the surface. The basesheet may be formed from one or more woven materials, nonwoven materials, cellulosic materials, and combinations of such materials. More specifically, the basesheet may be formed of nonwoven fibrous sheet materials that include meltblown, spunlace, coform, air-laid, bonded-carded web materials, hydroentangled materials, and combinations of such materials. Such materials can be made of synthetic or natural fibers or a combination of such fibers. Typically, the basesheet will have a basis weight of from about 25 grams per square meter to about 120 grams per square meter and desirably from about 40 grams per square meter to about 90 grams per square meter.

The basesheet may be constructed of a coform material of polymer fibers and absorbent fibers having a basis weight of from about 45 to about 80 grams per square meter and desirably about 60 grams per square meter. Typically, such coform basesheets are constructed of a gas-formed matrix of thermoplastic polymeric meltblown fibers and cellulosic fibers. Various suitable materials may be used to provide the polymeric meltblown fibers, such as, for example, polypropylene microfibers. Alternatively, the polymeric meltblown fibers may be elastomeric polymer fibers such as those provided by a polymer resin. For instance, VISTAMAXX elastic olefin copolymer resin designated PLTD-1810, available from ExxonMobil Corporation (Houston, Tex.), or KRATON G-2755, available from Kraton Polymers (Houston, Tex.), may be used to provide stretchable polymeric meltblown fibers for the coform basesheets. Other suitable polymeric materials or combinations thereof may alternatively be utilized as known in the art.

The coform basesheet additionally may be constructed of various absorbent cellulosic fibers, such as, for example, wood pulp fibers. Suitable commercially available cellulosic fibers for use in the coform basesheets can include, for example, NF 405, which is a chemically treated bleached southern softwood Kraft pulp, available from Weyerhaeuser Co. (Washington, D.C.); NB 416, which is a bleached southern softwood Kraft pulp, available from Weyerhaeuser Co.; CR-0056, which is a fully debonded softwood pulp, available from Bowater, Inc. (Greenville, S.C.); Golden Isles 4822 debonded softwood pulp, available from Koch Cellulose (Brunswick, Ga.); and SULPHATATE HJ, which is a chemically modified hardwood pulp, available from Rayonier, Inc. (Jessup, Ga.). The relative percentages of the polymeric meltblown fibers and cellulosic fibers in the coform basesheet may vary over a wide range depending upon the desired characteristics of the wipes. For example, the coform basesheet may have from about 10 weight percent to about 90 weight percent, desirably from about 20 weight percent to about 60 weight percent, and more desirably from about 25 weight percent to about 35 weight percent of polymeric meltblown fibers based on the dry weight of the coform basesheet.

The anti-adherent formulation may be incorporated into the basesheet in an add-on amount of from about 50% (by weight of the basesheet) to about 800% (by weight of the basesheet). More specifically, the formulation may be incorporated into the basesheet in an add-on amount of from about 200% (by weight of the basesheet) to about 600% (by weight of the basesheet) or from about 400% (by weight of the basesheet) to about 600% (by weight of the basesheet). The formulation add-on amounts may vary depending on the composition of the basesheet.

The anti-adherent formulation contains a carrier, a quaternary ammonium compound, and a fatty alcohol. The combination of the quaternary ammonium compound and fatty alcohol provided a synergistic anti-adherent benefit against menses and or fecal material. Quaternary ammonium compounds are cationic whereas menses carries a predominantly negative charge. Based on the expected electrostatic interaction between the quaternary ammonium compound and menses, it is surprising that a quaternary ammonium compound would not bind to the menses and result in greater adherence of menses to the skin.

The anti-adherent formulation may include a quaternary ammonium compound selected from behentrimonium methosulfate, behentrimonium chloride, cetrimonium chloride, stearamidopropyl ethyldimonium ethosulfate, $C_{10-40}$ isoalkylamidopropylethyldimonium ethosulfate, cocotrimonium chloride, quaternium-79 hydrolyzed collagen, quaternium-80, quaternium-88, quaternium-95, polyquaternium-68, polyquaternium-78, polyquaternium-81, polyquaternium-82, and combinations thereof. In one desirable embodiment, the quaternary ammonium compound may be behentrimonium chloride. Desirably, the anti-adherent formulation may include from about 0.1% by weight to about 10.0% by weight of the quaternary ammonium compound. More desirably, the anti-adherent formulation may include from about 0.25% by weight to about 7.0% by weight of the quaternary ammonium compound.

The anti-adherent formulation also includes a fatty alcohol. The fatty alcohol is selected from lauryl alcohol, myristyl alcohol, cetyl alcohol, cetearyl alcohol, stearyl alcohol, arachidyl alcohol, behenyl alcohol, and combinations thereof. Desirably, the fatty alcohol may have between 12 and 22 carbon atoms per molecule. In one desirable embodiment, the fatty alcohol may be cetearyl alcohol. Desirably, the anti-adherent formulation may include from about 0.5% by weight to about 10.0% by weight of the fatty alcohol. More desirably, the anti-adherent formulation may include from about 0.8% by weight to about 8.0% by weight of the fatty alcohol.

As described above, the anti-adherent formulation may include a carrier. Non-limiting examples of suitable carrier materials include water; glycols such as propylene glycol, butylene glycol, and ethoxydiglycol; lower chain alcohols such as ethanol and isopropanol; glycerin and glycerin derivatives; natural oils such as jojoba oil and sunflower oil; synthetic oils such as mineral oil; silicone derivatives such as cyclomethicone, and other pharmaceutically acceptable carrier materials. As will be recognized by one skilled in the art, the relative amounts of carrier material and other components in the formulation that can be used in the formulation will be dictated by the nature of the formulation. The levels can be determined by routine experimentation in view of the disclosure provided herein.

The liquid formulation desirably contains water. The liquid formulation can suitably contain water in an amount of from about 40% by weight of the formulation to about 99.9% by weight of the formulation and more preferably from about 60% by weight of the formulation to about 99.9% by weight of the formulation. For instance, where the formulation is used in connection with a wet wipe, the formulation can suitably contain water in an amount of from about 75% by weight of the formulation to about 99% by weight of the formulation.

Additionally, the liquid anti-adherent formulation desirably contains a polyol to help stabilize the formulation. Desirably, this is propylene glycol, butylene glycol, or glycerin. The liquid anti-adherent formulation can suitably contain a polyol in an amount of from about 0.5% by weight of the formulation to about 5.0% by weight of the formulation.

When the anti-adherent formulation is used in connection with a wet wipe, the anti-adherent formulation may also include an anti-foaming agent. Desirably, the anti-foaming agent may be polydimethyl silicone emulsion such as SAG* 710 Silicone Antifoam Emulsion commercially available from Union Carbide. The liquid anti-adherent formulation can suitably contain the anti-foaming agent in an amount of from about 0.1% by weight of the formulation to about 0.2% by weight of the formulation.

Additionally, the anti-adherent formulation may include a compatible surfactant. The surfactant is selected from cationic surfactants, nonionic surfactants, zwitterionic surfactants, and combinations thereof. The anti-adherent formulation may suitably include one or more compatible surfactants in an amount of from about 0.01% by weight of the formulation to about 10% by weight of the formulation.

As described above, the surfactant may be a nonionic surfactant. Nonionic surfactants typically have a hydrophobic base such as a long chain alkyl group or an alkylated aryl group, and a hydrophilic chain comprising a certain number (e.g., 1 to about 30) of ethoxy and/or propoxy moieties. Examples of some classes of nonionic surfactants that can be used include, but are not limited to, ethoxylated alkylphenols, ethoxylated and propoxylated fatty alcohols, polyethylene glycol ethers of methyl glucose, polyethylene glycol ethers of sorbitol, ethylene oxide-propylene oxide block co-polymers, ethoxylated esters of fatty ($C_{8-18}$) acids, condensation products of ethylene oxide with long chain amines or amides, condensation products of ethylene oxide with alcohols, and combinations thereof.

Various specific examples of suitable nonionic surfactants for use in the anti-adherent formulation include, but are not limited to, methyl gluceth-10, PEG-20 methyl glucose distearate, PEG-20 methyl glucose sesquistearate, $C_{11-15}$ pareth-20, ceteth-8, ceteth-12, dodoxynol-12, laureth-15, PEG-20 castor oil, polysorbate 20, steareth-20, polyoxyethylene-10 cetyl ether, polyoxyethylene-10 stearyl ether, polyoxyethylene-20 cetyl ether, polyoxyethylene-10 oleyl ether, polyoxyethylene-20 oleyl ether, an ethoxylated nonylphenol, ethoxylated octylphenol, ethoxylated dodecylphenol, ethoxylated fatty ($C_{1-22}$) alcohol, including 3 to 20 ethylene oxide moieties, polyoxyethylene-20 isohexadecyl ether, polyoxyethylene-23 glycerol laurate, PEG-80 sorbitan laurate, polyoxyethylene-20 glyceryl stearate, PPG-10 methyl glucose ether, PPG-20 methyl glucose ether, polyoxyethylene-20 sorbitan monoesters, polyoxyethylene-80 castor oil, polyoxyethylene-15 tridecyl ether, polyoxy-ethylene-6 tridecyl ether, laureth-2, laureth-3, laureth-4, PEG-3 castor oil, PEG-12 dioleate, PEG-8 dioleate, and combinations thereof.

Additional nonionic surfactants that can be used include water soluble alcohol ethylene oxide condensates, such as the condensation products of a secondary aliphatic alcohol containing between about 8 to about 18 carbon atoms in a straight or branched chain configuration condensed with between about 5 to about 30 moles of ethylene oxide. Such nonionic surfactants are commercially available under the trade name TERGITOL from Union Carbide Corporation (Danbury, Conn.). Specific examples of such commercially available nonionic surfactants of the foregoing type are $C_{11-15}$ secondary alkanols condensed with either 9 moles of ethylene oxide (TERGITOL 15-S-9) or 12 moles of ethylene oxide (TERGITOL 15-S-12).

Other suitable nonionic surfactants include the polyethylene oxide condensates of one mole of alkyl phenol containing from about 8 to 18 carbon atoms in a straight or branched chain alkyl group with about 5 to 30 moles of ethylene oxide. Specific examples of alkyl phenol ethoxylates include nonyl condensed with about 9.5 moles of ethylene oxide per mole of nonyl phenol, dinonyl phenol condensed with about 12 moles of ethylene oxide per mole of phenol, dinonyl phenol condensed with about 15 moles of ethylene oxide per mole of phenol, and diisooctylphenol condensed with about 15 moles of ethylene oxide per mole of phenol. Commercially available nonionic surfactants of this type include Igepal CO-630 (a nonyl phenol ethoxylate) from ISP Corp. (Wayne, N.J.). Suitable nonionic ethoxylated octyl and nonyl phenols include those having from about 7 to about 13 ethoxy units. Such compounds are commercially available under the trade name TRITON X from Union Carbide (Danbury, Conn.).

Alkyl polyglycosides may also be used as a nonionic surfactant in the anti-adherent formulation. Suitable alkyl polyglycosides are known nonionic surfactants that are alkaline and electrolyte stable. Alkyl mono and polyglycosides are prepared generally by reacting a monosaccharide or a compound hydrolyzable to a monosaccharide with an alcohol such as a fatty alcohol in an acid medium.

Suitable zwitterionic surfactants for use in the anti-adherent formulation include, for example, alkyl amine oxides, silicone amine oxides, and combinations thereof. Various specific zwitterionic surfactants for use in the anti-adherent formulation include, for example, 4-[N,N-di(2-hydroxyethyl)-N-octadecylammonio]-butane-1-carboxylate, 5-[S-3-hydroxypropyl-5-hexadecylsulfonio]-3-hydroxypentane-1-sulfate, 3-[P,P-diethyl-P-3,6,9-trioxatetradexopcylphosphonio]-2-hydroxypropane-1-phosphate, 3-[N,N-dipropyl-N-3-dodecoxy-2-hydroxypropylammonio]-propane-1-phosphonate, 3-(N,N- dimethyl-N-hexadecylammonio)propane-1-sulfonate, 3-(N,N-dimethyl-N-hexadecylammonio)-2-hydroxypropane-1-sulfonate, 4-[N,N-di(2-hydroxyethyl)-N-(2-hydroxydodecyl)ammonio]-butane-1-carboxylate, 3-[S-ethyl-S-(3-dodecoxy-2-hydroxypropyesulfonio]-propane-1-phosphate, 3-[P,P-dimethyl-P-dodecylphosphonio]-propane-1-phosphonate, 5-[N,N-di(3-hydroxypropyl)-N-hexadecylammonio]-2-hydroxy-pentane-1-sulfate, and combinations thereof.

Suitable cationic surfactants for use in the anti-adherent formulation include, for example, alkyl ammonium salts, polymeric ammonium salts, alkyl pyridinium salts, aryl ammonium salts, alkyl aryl ammonium salts, silicone quaternary ammonium compounds, and combinations thereof. Specific examples of cationic surfactants include behenyltrimonium chloride, stearlkonium chloride, distearalkonium chloride, chlorohexidine digluconate, polyhexamethylene biguanide (PHMB), cetyl pyridinium chloride, benzethonium chloride, benzalkoniumchloride, and combinations thereof.

In addition to the components described herein, the anti-adherent formulation may also include a pH adjuster, fragrance, preservative, dye, corrosion inhibitor, builder, cleansing solvent, and other components known to be useful in personal care formulations.

As described above, the anti-adherent formulation provides resistance from menses and or fecal material sticking to the hair and skin of a user. Thus, when the anti-adherent formulation is placed on a surface such as skin, and menses or fecal material then contacts the skin, less of the menses remains on the skin. The menses leave-on percentage is defined as calculated per the test method described below. Desirably, the menses leave-on percentage is less than about 7.4%.

Test Method
Menses Leave-On Percentage

The Menses Leave-On Percentage was calculated using simulated skin and simulated menses. Vitro-Skin® samples commercially available from IMS Testing Group (Portland, Me.) were prepared by cutting to a dimension of 4×4 cm. The Vitro-Skin® samples were adhered to a 5×5 cm glass slide. 100 mg of each prospective anti-adherent formulation is added to Vitro-Skin® and spread evenly across the surface using a glass rod. For applications using wipes, a 15.2×18.8 cm wet wipe constructed of hydroknit wetted with a prospective anti-adherent formulation was folded in half, four times. Holding the glass slide with one hand and the wet wipe in the other the wipe was pressed to the Vitro-Skin® using firm, even pressure when wiping across the top half of the skin. Using the same technique, the bottom half of the skin was wiped. This was repeated so that the Vitro-Skin® was wiped four times on the top and bottom half of the Vitro-Skin®. The Vitro-Skin® was allowed to dry for a set amount of time. The Vitro-Skin® was allowed to dry for at least 60 seconds following treatment application. Untreated Vitro-Skin® was used as a negative control.

The Vitro-Skin®, Kotex® UltraThin (Regular) feminine pads commercially available from Kimberly-Clark Corporation (Neenah, Wis.), and menses simulant were placed in a humidity chamber at 85% humidity and 32° C. and allowed to acclimate for 1 hour. After 1 hour the mass of each Vitro-Skin® and feminine pad was recorded. Then, 1000 mg of menses simulant was applied to the Vitro-Skin® and allowed a contact time of 60 seconds. A feminine pad was placed on the Vitro-Skin® and a 409 g mass weight (10 cm×15 cm) was placed onto the feminine pad. The feminine pad and weight were left on the Vitro-Skin® for 60 seconds. In the case of multiple insults, after the initial 60 seconds, 1000 mg of menses simulant was applied to the Vitro-Skin® and allowed a contact time of 60 seconds before the feminine pad and weight were placed on the Vitro-Skin® for an additional 60 seconds. This was repeated for the desired amount of insults. For example, in the case of four insults, this procedure was repeated four times.

After the desired amount of insults and application of the feminine pad, the feminine pad and weight were removed and the mass of the Vitro-Skin® and feminine pad was recorded. The percent menses left behind on the skin and feminine pad was calculated by dividing the mass left behind on Vitro-Skin® by the sum of the mass left behind on the pad and the mass left behind on Vitro-Skin®. The mass left behind on Vitro-Skin® and pads was determined by subtracting final mass values from baseline values.

EXAMPLES

Example 1

In this example, exemplary anti-adherent formulations A-K were prepared by using the illustrated amount, of a fatty alcohol (FA) and a quaternary ammonium compound (QA). Each formulation included 1.99% by weight butylene glycol and the remainder of an ethanol solvent. Comparative formulations A-I were prepared with only a fatty alcohol and comparative formulations. Each of the formulations was tested with a single insult of menses as described in the Menses Leave-On Percentage Test described above to determine the menses leave-on percentage. Table 1 illustrates the type and amount of fatty alcohol (FA), the type and amount a quaternary ammonium compound (QA), and the menses leave-on percentage for each formulation.

TABLE 1

Exemplary and Comparative Formulations

| Formulation | QA | QA WT % | FA | FA WT. % | Menses Leave-On Percentage (%) |
|---|---|---|---|---|---|
| A1 | behentrimonium chloride | 2.58 | caprylic alcohol | 2.12 | 12.15 |
| A2 | behentrimonium chloride | 2.58 | 1-decanol | 2.57 | 13.18 |
| A3 | behentrimonium chloride | 2.58 | lauryl alcohol | 3.03 | 7.35 |
| A4 | behentrimonium chloride | 2.58 | myristyl alcohol | 3.48 | 7.04 |
| A5 | behentrimonium chloride | 2.58 | cetyl alcohol | 3.94 | 6.77 |

TABLE 1-continued

Exemplary and Comparative Formulations

| Formulation | QA | QA WT % | FA | FA WT. % | Menses Leave-On Percentage (%) |
|---|---|---|---|---|---|
| A6 | behentrimonium chloride | 2.58 | cetearyl alcohol | 4.15 | 5.83 |
| A7 | behentrimonium chloride | 2.58 | stearyl alcohol | 4.4 | 5.46 |
| A8 | behentrimonium chloride | 2.58 | arachidyl alcohol | 4.85 | 6.02 |
| A9 | behentrimonium chloride | 2.58 | behenyl alcohol | 5.3 | 5.74 |
| B6 | cocotrimmonium chloride | 1.74 | cetearyl alcohol | 4.15 | 3.28 |
| C6 | cetrimonium chloride | 2.05 | cetearyl alcohol | 4.15 | 3.24 |
| D6 | $C_{10-40}$ isoalkylamidopropylethyldimonium ethosulfate | 4.07 | cetearyl alcohol | 4.15 | 4.08 |
| E6 | polyquaternium-68 | 1.01 | cetearyl alcohol | 4.15 | 11.59 |
| F6 | polymethacrylamidopropyltrimonium chloride | 1.41 | cetearyl alcohol | 4.15 | 10.81 |
| G6 | polyquaternium-82 | 0.91 | cetearyl alcohol | 4.15 | 4.31 |
| H6 | polyquaternium-81 | 0.72 | cetearyl alcohol | 4.15 | 3.78 |
| I6 | polyquaternium-78 | 0.59 | cetearyl alcohol | 4.15 | 3.76 |
| J6 | polyquaternium-88 | 3.38 | cetearyl alcohol | 4.15 | 2.89 |
| K6 | quaternium-95 | 5.49 | cetearyl alcohol | 4.15 | 4.033 |
| L6 | quaternium-79 hydrolyzed collagen | 0.60 | cetearyl alcohol | 4.15 | 6.75 |
| M6 | quaternium-80 | 2.50 | cetearyl alcohol | 4.15 | 1.61 |
| Comparative 1 | — | — | caprylic alcohol | 2.12 | 13.33 |
| Comparative 2 | — | — | 1-decanol | 2.57 | 12.63 |
| Comparative 3 | — | — | lauryl alcohol | 3.03 | 11.39 |
| Comparative 4 | — | — | myristyl alcohol | 3.48 | 11.55 |
| Comparative 5 | — | — | cetyl alcohol | 3.94 | 9.56 |
| Comparative 6 | — | — | cetearyl alcohol | 4.15 | 7.42 |
| Comparative 7 | — | — | stearyl alcohol | 4.4 | 10.41 |
| Comparative 8 | — | — | arachidyl alcohol | 4.85 | 4.344 |
| Comparative 9 | — | — | behenyl alcohol | 5.3 | 7.03 |
| Comparative A | behentrimonium chloride | 2.58 | — | — | 12.57 |
| Comparative B | cocotrimmonium chloride | 1.74 | — | — | 15.23 |
| Comparative C | cetrimonium chloride | 2.05 | — | — | 16.3 |
| Comparative D | C10-40 isoalkylamidopropylethyldimonium ethosulfate | 4.07 | — | — | 13.13 |
| Comparative F | polyquaternium-68 | 1.01 | — | — | 11.9 |
| Comparative F | polymethacrylamidopropyltrimonium chloride | 1.41 | — | — | 12.68 |
| Comparative G | polyquaternium-82 | 0.91 | — | — | 13.04 |
| Comparative M | quaternium-80 | 2.50 | — | — | 8.64 |
| Comparative H | polyquaternium-81 | 0.72 | — | — | 12.14 |
| Comparative I | polyquaternium-78 | 0.59 | — | — | 12.24 |
| Comparative J | polyquaternium-88 | 3.38 | — | — | 10.10 |
| Comparative K | quaternium-95 | 5.49 | — | — | 10.85 |
| Comparative L | quaternium-79 hydrolyzed collagen | 0.6 | — | — | 11.42 |

As can be seen by Exemplary Formulations, there is a synergy provided by providing a formulation with both a fatty alcohol and a quaternary ammonium compound that provides an effective amount of anti-adherence. As can be seen by the comparative examples, the fatty alcohol or quaternary ammonium compounds alone did not provide the same efficacy as when combined.

In addition, in Exemplary Formulations C through 0, the fatty alcohol has between 12 and 22 carbon atoms per molecule and has a menses leave-on percentage of less than 7.4%. While not required, it is preferable for the fatty alcohol have between 12 and 22 carbon atoms per molecule to provide the desired efficacy.

Example 2

In this example, a formulation was prepared using the amounts illustrated in Table 2 and applied to a hydroknit wipe. The formulation described in Table 2 contains approximately 1.72% of a fatty alcohol, cetyl alcohol, and 2.0% of a quaternary ammonium compound, behentrimonium methosulfate. The formulation was tested using the Menses Leave-On Percentage Test described above and found to provide a menses leave-on percentage of 3.10%.

TABLE 2

Exemplary Wipe Formulation

| Supplier(s) | Trade Name | INCI Name | Final Activity % in Formulation |
|---|---|---|---|
|  | Water | Water | 93.1800 |
| Croda | Incroquat Behenyl TMS-50-PA | Behentrimonium Methosulfate | 2.0000 |
|  |  | Cetyl Alcohol | 1.7200 |
|  |  | Butylene Glycol | 0.2800 |
| Symrise | Symdiol 68 | 1,2-Hexanediol | 0.3000 |
|  |  | Caprylyl Glycol | 0.3000 |
| Rita | Butylene Glycol | 1, 3 Butylene Glycol | 2.0000 |
| Active Organics | Actiphyte of Burdock Root BG50P | Butylene Glycol | 0.0395 |
|  |  | Water | 0.0395 |
|  |  | Arctium Lappa Root Extract | 0.0200 |
|  |  | Phenonip | 0.0010 |
| Active Organics | Actiphyte of Dandelion BG50P | Butylene Glycol | 0.0395 |
|  |  | Water | 0.0395 |
|  |  | Taraxacum Officinale (Dandelion) Leaf Extract | 0.0200 |
|  |  | Phenonip | 0.0010 |
| Purac | Lactic Acid | Lactic Acid | 0.0176 |
|  |  | Water | 0.0024 |
|  |  | Total | 100.0000 |

While the anti-adherent formulation has been described in detail with respect to specific aspects thereof, it will be appreciated that those skilled in the art, upon attaining an understanding of the foregoing, may readily conceive of alterations to, variations of and equivalents to these formulations. Accordingly, the scope of the present invention should be assessed as that of the claims and any equivalents thereto.

The invention claimed is:

1. An anti-adherent formulation having anti-adherent activity comprising:
a carrier,
from about 0.1% by weight to about 10% by weight of a quaternary ammonium compound; and
from about 0.5% by weight to about 10% by weight of a fatty alcohol;
wherein the anti-adeherent formulation has menses leave-on percentage of less than about 7.4%.

2. The anti-adherent formulation of claim 1 wherein the quaternary ammonium compound is selected from behentrimonium methosulfate, behentrimonium chloride, behentrimoniumsulfate, cetrimonium chloride, stearamidopropyl ethyldimonium ethosulfate, $C_{10\text{-}40}$ isoalkylamidopropylethyldimonium ethosulfate, cocotrimonium chloride, quaternium-79 hydrolyzed collagen, quaternium-80, quaternium-88, quaternium-95, polyquaternium-68, polyquaternium-78, polyquaternium-81, polyquaternium-82, and combinations thereof.

3. The anti-adherent formulation of claim 2 wherein the quaternary ammonium compound is selected from behentrimonium methosulfate, behentrimonium chloride, and quaternium-80.

4. The formulation of claim 1 wherein the fatty alcohol is selected from lauryl alcohol, myristyl alcohol, cetyl alcohol, cetearyl alcohol, stearyl alcohol, arachidyl alcohol, behenyl alcohol, and combinations thereof.

5. The anti-adherent formulation of claim 4 wherein the fatty alcohol has between 12 and 22 carbon atoms per molecule.

6. The anti-adherent formulation of claim 4 wherein the fatty alcohol comprises cetearyl alcohol.

7. The anti-adherent formulation of claim 1 further comprising from about 0.5% to about 5.0% by weight polyol.

8. The anti-adherent formulation of claim 1 wherein the formulation includes from about 0.25% by weight to about 7.0% by weight of the quaternary ammonium compound.

9. The anti-adherent formulation of claim 1 wherein the carrier is water, and wherein the anti-adherent formulation contains between about 65% and about 99% by weight of the carrier.

10. A wet wipe comprising:
a wipe substrate; and
a liquid formulation containing:
a carrier,
from about 0.1% by weight to about 10.0% by weight of a quaternary ammonium compound; and
from about 0.5% by weight to about 10.0% by weight of a fatty alcohol;
wherein the liquid formulation has menses leave-on percentage of less than about 7.4%.

11. The wet wipe of claim 10 wherein the quaternary ammonium compound is selected from behentrimonium methosulfate, behentrimonium chloride, behentrimonium-sulfate, cetrimonium chloride, stearamidopropyl ethyldimonium ethosulfate, $C_{10\text{-}40}$ isoalkylamidopropylethyldimonium ethosulfate, cocotrimonium chloride, quaternium-79 hydrolyzed collagen, quaternium-80, quaternium-88, quaternium-95, polyquaternium-68, polyquaternium-78, polyquaternium-81, polyquaternium-82, and combinations thereof.

12. The wet wipe of claim 11 wherein the quaternary ammonium compound is selected from behentrimonium methosulfate, behentrimonium chloride, and quaternium-80.

13. The wet wipe of claim 10 wherein the fatty alcohol is selected from lauryl alcohol, myristyl alcohol, cetyl alcohol, cetearyl alcohol, stearyl alcohol, arachidyl alcohol, behenyl alcohol, and combinations thereof.

14. The wet wipe of claim 13 wherein the fatty alcohol comprises cetearyl alcohol.

15. The wet wipe of claim 10 wherein the formulation includes from about 0.25% by weight to about 7.0% by weight of the quaternary ammonium compound.

16. The wet wipe of claim 10 wherein the carrier is water, and wherein the liquid formulation contains between about 65% and about 99% by weight of the carrier.

17. The wet wipe of claim 10 further comprising from about 0.5% to about 5.0% by weight polyol.

* * * * *